United States Patent [19]

Bout

[11] 4,178,365

[45] Dec. 11, 1979

[54] METHOD OF PREPARING AN ANTIPARASITIC IMMUNOLOGICAL AGENT, THE PRODUCT OBTAINED, AND ITS APPLICATION

[75] Inventor: Daniel Bout, Le Maisnil, France

[73] Assignees: Institut National de la Sante et de la Recherche Medicale - Centre de Technologie Biomedicale I.N.S.E.R.M., Paris; Institut Pasteur, Lille, both of France

[21] Appl. No.: 814,211

[22] Filed: Jul. 11, 1977

[51] Int. Cl.² .............................................. A61K 39/00
[52] U.S. Cl. ........................................................ 424/88
[58] Field of Search .......................................... 424/88

[56] References Cited

U.S. PATENT DOCUMENTS 3,860,483   1/1975   Senft .................................... 424/88

OTHER PUBLICATIONS

Chem. Abst. 8th Collective Index vol. 66–75 (1967–1971) p. 28048s.

*Primary Examiner*—Sam Rosen
*Attorney, Agent, or Firm*—Martin A. Farber

[57] ABSTRACT

This invention relates to a method of preparing an immunological agent. It also concerns the product obtained and its application.

The method is characterized by:
  contacting a parasiticidal drug with a previously defined total extract of antigens of the corresponding parasite in such a manner that the previously defined target antigens attach themselves to the drug,
  thereupon, possibly, effecting a removal of the target antigens from the said drug.

11 Claims, No Drawings

METHOD OF PREPARING AN ANTIPARASITIC IMMUNOLOGICAL AGENT, THE PRODUCT OBTAINED, AND ITS APPLICATION

This invention relates to a method of preparing an immunological agent. It also concerns the product obtained as well as its application.

In the battle against parasitic pandemics, few curative or prophylactic agents are completely effective, whether there be concerned chemotherapy or vaccinotherapy.

In the former case, in the present state of our knowledge, schistosomiasis is treated only by chemotherapy, in particular by NIRIDAXOLE which is marketed under the brand name "Ambilhar." This product cures the disease but does not protect against subsequent infection. The infestation takes place transcutaneously: infesting larvae known as cercariae, penetrate the skin, are transformed and while growing arrive at the liver and mature a few weeks after the transcutaneous infestation. The males and females couple whereupon the females lay their eggs in the periintestinal veins (intestinal schistosomiasis) or perivesicular veins (urinary schistosomiasis). These eggs pass through the intestinal or vesical wall, are eliminated to the outside and liberate a larva which infests an aquatic mollusk. In this mollusk, this larva multiplies and is transformed into cercariae which then infest man.

In summary, chemotherapy does not immunize.

In the latter case, that of vaccinotherapy, as a general rule, the method of protecting an individual from bacterial or viral infectious agents consists of immunizing against the antigens of these infectious agents. However, in the case of the parasitic ailments, particularly schistosomiasis, it has not yet been possible to produce an effective protective immunity response.

In actual practice, the only weapon available at the present time is chemotherapy which, although curative, cannot prevent reinfection.

The inventor has attacked the problem from an immunological standpoint within the scope of schistosomiasis or bilharziosis, an ailment which at present is suffered by about 300,000,000 persons. It is known that the schistosomicidal drugs act at the target sites of the parasite, which sites consist of antigens, which will hereinafter be referred to as target antigens, and which are molecular structures which are essential for the integrity and survival of the parasite. The inventor has used known schistosomicidal drugs, as ligands, by particular in affinity chromatography, in order to try to isolate the target antigens, the immunogenic power of which has been established either by active immunization or passive transfer of antibodies. In other words, the invention comprises a new antiparasitic immunological agent formed of schistosome extract and in particular of target antigens of schistosomicidal drugs.

The invention furthermore concerns the application of these agents to in particular the preventive treatment of schistosomiasis. As a matter of fact, the target antigens injected into the organism result there in the formation of antibodies which are directed against these target antigens and are protectors from schistosomiasis. It should, as a matter of fact, be pointed out that up to the present time it has not been possible to obtain antibodies which truly protect against the parasite, in particular when a total extract of parasite antigens, formed by the supernatant of crushed parasites in, for instance, a solution of NaCl is used as immunizing antigen.

The invention also relates to a method of preparation which is characterized by:

contacting a schistosomicidal drugs with a total extract of schistosome antigens so that the target antigens are fixed on the drugs then possibly eluting the target antigens so as to isolate them. More precisely, the process consists in using an affinity chromatography in which the ligand is formed of a schistosomicidal drug which serves as binding agent for the target antigens, the ligand being immobilized on an insoluble support so that target antigens are retained and then eluted by a suitable agent and thereupon injected in animals in whose organism they produce the formation of protective antibodies which are effective against schistosomiasis.

One can also use affinity chromatogrphy in which the ligand is a non-fixed non-immobilized schistosomicidal drug, which is used however under conditions of supersaturated solution such that a given amount of ligand remains insoluble in the process of isolation of the target antibodies. The dry extract formed of the schistosomicidal ligand bearing the target antigens can be used for the treatment of schistosomiasis after suspension in a suitable solvent for instance.

When considering this result, it should be recalled that the total antigens of schistosome which were injected in these same animals did not result in any synthesis of protective antibodies, which shows the importance of the method of the invention.

The invention will be better understood on basis of the following examples which indicate, in particular, a few therapeutic applications effected in the experimental stage on animals.

The immunochemical analysis showed that a schistosome represented a very complicated mixture of antigens. Among the numerous methods of study employed, immmunoselectrophoresis made it possible to show at least 25 precipitating systems some of which exhibit an allergenic nature or support enzymatic activity. Among these antigens of important biological function there are the target antigens of the schistosomicidal drugs for some of which an activity-inhibiting enzyme of the parasite has been shown. These drugs have been used as ligands using the principals of affinity chromatography in order to try to isolate the target antigens and characterize their enzymatic activities and their location at the level of the parasite as well as their immunogenic power.

MATERIAL AND METHODS

1. Obtaining target antigens

The target antigens are isolated from a total antigen extract of schistosomes (Schistosoma mansoni) prepared from adult worms collected from hamsters, if not otherwise specified. 3500 freshly collected worms are crushed in 2 ml of 0.5 M NaCl, frozen and thawed by crushing in a Potter apparatus, and then centrifuged at 40,000 g for 30 minutes. The supernatant is used as total antigen.

The schistosomicidal drugs used as ligands are NIRIDAZOLE (Ciba, 32,644 Ba), THIOSINAMINE (Fluka), ASTIBAN (Roche), EMETINE CHLOROHYDRATE (Rhone Poulenc) and AMPHOTALIDE (6171 Rhone Poulenc).

Affinity Chromatography

Preparation of the immobilized ligands

The supports known under the commercial name AH and CH-Sepharose (Pharmacia —Sweden) permit the synthesis of specific absorbents in which the ligand is separated from the support by a chain of 6 carbon atoms. The ligand is fixed to the support by a single-step coupling reaction to carbodiimide. CH-Sepharose has free carboxyl groups which can be used to couple ligands to free primary amine groups. AH-Sepharose has free primary amine groups which can be used for coupling carboxyl groups. The procedure for coupling to the carbodiimide recommended by Pharmacia is used. Niridazole (30 mg/10 ml of water), Thiosinamine (30 mg/10 ml of water), and Amphotalide (30 mg/10 ml of dioxane) are coupled to 2 g of CH-Sepharose gel. Astiban (30 mg/15 ml of water) and the double tartrate of antimony and potassium (30 mg/10 ml of water) are coupled to 2 g of AH-Sepharose gel. The operating procedure used for each drug is the same. The lyophilized powder of AH or CH-Sepharose is weighed and then swollen in an excess of 0.5 M NaCl solution. In order to eliminate lactose and dextran, the gel is washed with the 0.5 M NaCl solution and then with distilled water in order to eliminate the NaCl. The ligand solution is added to the gel. The pH of the suspension is adjusted to between 4.5 and 6. A final liquid-gel proportion (2:1) is suitable for a mild agitation which is effected at laboratory temperature. The carbodiimide powder is added to a final concentration of 0.1 M. The pH is maintained between 4.5 and 6 for 1 hour. The reaction is continued for 24 hours at laboratory temperature. The gel is washed in succession in alkaline and acid buffer solutions containing molar NaCl. If dioxane was used for the dissolving of the ligand, it is necessary to wash the gel with this solvent. The gel is finally washed with distilled water.

Isolation of target antigens by means of these immobilized ligands

The crude antigen extract of schistosome (3500 worms $\neq$/ 20 mg dry weight) is passed over the 2 ml column of gel. The column is washed with a solution of 0.5 M NaCl until the optical density at 280 nm is zero. The fixed antigen coponents are eluted with a buffer of glycine —0.2 M HCl, 0.5 M NaCl, pH 2.8. The eluate is immediately neutralized in a 1 M phosphate buffer of a pH of 8, and then dialyzed against water. The quantity of product obtained is evaluated in optical density at 280 nm.

Affinity chromatography on non-immobilized ligands

An amount of 1.5 mg of drug is present under the experimental conditions in insoluble form during the contact with the antigen extract of the worm and during the washings with saturated solutions of the drug. The antigen extract (0.1 ml = 1 mg dry weight) of schistosomes (collected from mice) (for the immunization of mice) or from hamsters (for the immunization of rabbits) is contacted with 2 mg Niridazole, 5 mg Thiosinamine, 10 mg of antimony-potassium tartrate, 40 mg of Astiban, 15 mg of Emetine Hydrochloride, and 3 mg of Amphotalide. After contact for 1 hour at 37° C. and for 30 minutes at laboratory temperature, the insoluble drug is washed 3 times with 10 ml of saturated solution of the drug in question. The target antigen ligand which is obtained will serve for the immunization of mice or rabbits.

2. Immunochemical characterization and parasitic localization of the target antigens This study is carried out employing the immune serums of rabbits which have been injected with the different target antigens.

Immunization of rabbits

An amount of insoluble drug, incubated with the antigen extract of schistosome (the entire insoluble matter obtained under the conditions described) was injected in rabbits; VAITUKAITIS et al.

A blood sample was taken on the 35th day ($S_1$), the 50th day ($S_2$) and the 80th day ($S_3$).

For the immunoselectrophoresis and immunofluorescence studies which were carried out, the immune serums (I.S.) were previously absorbed by host antigens. The absorption was effected by adding 10 mg of lyophilized hamster serum and 10 mg of lyophilized hamster liver to 1 ml of immune serum. After incubation for 2 hours at 37° C., the mixture was incubated overnight at 4° C. and then centrifuged. The supernatant liquid represents the absorbed I.S.

Study of the target antigens in immuno-precipitation

The conventional immunoelectrophoresis was carried out in accordance with the method described by Capron et al using the schistosome antigen extract and the different anti-target-antigen immune serums.

The bidimensional immunoelectrophoresis is based on the technique described by Laurell. Glass slides of 5 ×5 cm were used. The migration of the Sm antigen (2 mg) in a 1% agarose gel in Veronal buffer of a pH of 8.2 (Veronal sodium 16 g, 1 N HCl 22 ml water QSP 1000 ml) took place during two hours under a ddp of 12.5 volts at the edges of the slides. The second migration took place in an agarose gel containing the I.S. (agarose 1.3%, 2.34 ml; I.S. 1.16 ml) overnight under a ddp of 3 volts at the edges of the slides.

Evidencing the enzymatic activities the target antigens

The enzymatic activities (LDH, $G_6$, PDH, MDH, AlDH, alpha- and beta-carboxylesterases) were determined in accordance with a technique developed by URIEL at the level of the precipitates obtained in double diffusion in gel between the Sm antigen and the different target antigen immune serums.

Localization of the target antigens of the schistosome by immunofluorescence The schistosome sections were prepared and treated in the following manner. After three washings in the buffered physiological serum, the worms which were taken from the hamster were fixed in "BOUIN-HOLLANDE-SUBLIME," dehydrated in baths of ethyl alcohol of increasing concentrations, treated with butyl alcohol, and enclosed in paraffin. The blocks were cut into sections of 5 to 6μ in thickness, which are fixed on microscope slides. These worm sections were dewaxed, washed in buffered physiological serum and incubated for 30 minutes at 37° C. with the anti-target-antigen rabbit immune serum, diluted to 1:20 and then to 1:160. The slides were then washed in buffered physiological serum and incubated for 30 minutes at 37° C. with fluorescent antibodies anti rabbit immunoglobulins produced in goat (Pasteur Institute) diluted to 1:50. The slides were washed and subjected to a contra-coloring with Evans Blue. As specificity control, the inhibition of fluorescence was effected by using the anti-target-antigen immune serum previously absorbed with the schistosome total antigen extract.

3. Study of the immunogenicity of the target antigens (a) Immunization of rats

Three-month old Fischer rats weighing 180 g were immunized in accordance with the following procedure:

At d-55 (55 days before the infestation), an injection of target antigens was effected intradermally (target antigens 50 micrograms—diphtheria toxoid of the Pasteur Institute 40 μ—Freunds completed adjuvant 40 μl).

At d-38, subcutaneous injection of the same suspension.

At d-24, injection of the same suspension in plantar pads.

At d-O, infestation by 800 cercariae.

The rats were bled at d-45 ($S_1$), d-30 ($S_2$), d-17 ($S_3$), d-4 ($S_4$) d-22 ($S_5$).

Rats receiving the same suspension without target antigens serve as controls.

The collection of the worms was effected at d-22 by hepatic perfusion. The male, female, and immature worms were counted.

The study of the cytotoxicity of the serums was effected in accordance with the procedure used by Capron et al and described by CLEGG and SMITHERS.

(b) Immunization of mice

An amount of insoluble drug was incubated with the antigen extract of Schistosoma mansoni (1/10 of the insoluble amount obtained under the conditions described for one mouse) is injected (ore injection) in the plantar pads of C 57 black mice of 18 g, of 5 weeks old. This dose of ligand-antigen was placed in suspension in 0.2 ml of 0.8% NaCl, 0.1 g of Tween 80, and 25 μof A. C. F.

Control mice received 0.1 g of Tween 80 and 25 μl of A.C.F. Other drug control mice received the same quantity of orginal drug without antigen.

The mice were infested 15 days later by 60 cercariae, and were bled and perfused 70 days later. The male and female worms collected by hepatic perfusion are counted.

(c) Passive transfer of anti-target-antigen antibodies in mice

The C 57 mice received 0.3 ml of anti-target-antigen rabbit immune serum intravenously in the tail and 0.25 ml of fresh healthy rabbit serum as a source of supplement intraperitoneally. The infestation by 60 cercariae took place one hour after these injections. The mice were bled and sacrificed 60 days after the infestation. The worms were counted.

RESULTS

1. Immunochemical study of the target antigens (a) Isolation 2 ml of Sepharose-ligand gel was mixed with 20 mg of Schistosoma mansoni antigen extract and permitted the obtaining of the following target antigen quantities, evaluated at 280 nm:

| CH-Sepharose | - Niridazole | :160 μg target antigen |
|---|---|---|
| | - Thiosinamine | 290 μg |
| AH-Sepharose | - antimony/potassium tartrate | :1.65 mg |
| | - Astiban | 290 μg |
| CH-Sepharose | - Emetine | :260 μg |
| | - Amphotalide | 80 μg |

AH-and CH-Sepharose not coupled to ligands do not fix antigen non-specifically.

(b) Immunoelectrophoretic chart of the target antigens

The anti-target-antigen immune serums plotted, in conventional or bidimensional immunoselectrophoresis against an antigen extract of Schistosoma mansoni permit the obtaining for each of them of a specific profile comprising one or more precipitant systems. The anti-target antigen immune serum of Amphotalide does not contain detectable precipitant target antigens.

Comparatively, the anti-S-mansoni-antigen immune serum makes it possible to note in bidimensional immunoselectrophoresis more than 40 precipitating systems.

(c) Enzymatic activities of the target antigens

They are reported in Table (I).

(d) Localization of the target antigens at the level of the parasite

The anti-target-antigen immune serum of Niridazole shows a diffuse fluorescence at the level of the parenchyma of the schistosome, primarily in males whose tubercles are also fluorescent.

The anti-target antigen immune serum of Thiosinamine shows a fluorescence which is exclusively limited to the cell bed of the digestive cecum, with the exception of the cellular nuclei. The anti-target-antigen immune serum of antimony/potassium tartrate shows a similar fluorescence.

The anti-target-antigen immune serum of Astiban shows a fluorescence which is exclusively limited to the superficial cell bed of the cecum, sparing the nuclei, and of discontinuous type. The anti-target-antigen immune serum of Emetine shows a total fluorescence of the superficial cell bed of the cecum. The anti-target-antigen immune serum of Amphotalide shows only a diffuse fluorescence of the parenchyma.

TABLE I

| rabbit anti-target-antigen immune serum of: | Immunoelectrophoresis (IEP)* | | Enzymatic activities **detected at the level of precipitating systems | Localization of the target antigens in immunofluorescence |
|---|---|---|---|---|
| | CONVENTIONAL No. of arcs | BIDIMENSIONAL No. of peaks | | |
| NIRIDAZOLE | 1 | 1 | | PARENCHYMA |
| THIOSINAMINE | 3 | 4 | G6 PDH AlDH | CECUM |
| DOUBLE TARTRATE OF ANTIMONY AND POTASSIUM | 4 | 6 | MDH G6PDH Alpha-carboxyl-esterase | CECUM |
| ASTIBAN | 3 | 3 | G6 PDH Al.DH | CECUM |
| EMETINE | 1 | 3 | G6 PDH | CECUM |

TABLE I-continued

| rabbit anti-target-antigen immune serum of: | Immunoelectrophoresis (IEP)* | | Enzymatic activities **detected at the level of precipitating systems | Localization of the target antigens in immunofluorescence |
|---|---|---|---|---|
| | CONVENTIONAL No. of arcs | BIDIMENSIONAL No. of peaks | | |
| AMPHOTALIDE | 0 | 0 | 0 | PARENCHYMA |

LEGEND OF TABLE I:
*Number of arcs obtained in conventional IEP and number of peaks obtained in bidimensional IEP between a total extract of Schistosoma mansoni and the anti-target-antigen immune serums.
**Number of enzymatic activities revealed at the level of the precipitating systems obtained between the total schistosome extract and the anti-target-antigen immune serums.
***Localization of the target antigens effects with the different anti-target-antigen immune serums.

2. Immunobiological Study (a) Study of the immunological phenomena in immunized rats In vitro study of the cytotoxicity of the serums The serums ($S_1$ to $S_5$) are collected separately to determine their lethal effect on the schistosomes and the schistosomules. Each experiment is carried out twice. The different serums have no lethal effect on the adult schistosomes. The rat serums ($S_5$) immunized with the target antigens of Emetine or Thiosinamine cause 40 and 27.5% mortality respectively. The infested controls and the healthy controls give only 20 and 7% mortality respectively.

Counting of the worms collected by hepatic perfusion.

The number of male, female, and immature worms is noted. The results are set forth in Table II:

TABLE II

| | males | females | immature | total |
|---|---|---|---|---|
| Rats controlled (4) * | 19.50 ± 3 | 16 ± 3.74 | 2.75 ± 1.71 | 38.25 ± 5.38 |
| Rats immunized with target antigens of: DOUBLE TARTRATE OF ANTIMONY AND POTASSIUM (4) * | 3.25 ± 3.20 | 3 ± 2.16 | 1.25 ± 0.96 | 7.50 ± 5.07 |
| AMPHOTALIDE (4) * | 7.50 ± 3.32 | 5.50 ± 5.07 | 1.75 ± 1.71 | 14.75 ± 9.60 |

LEGEND OF TABLE II:
Average (± standard difference) of the male, female, immature, and total worms, collected by hepatic perfusion, of rats immunized with the different target antigens and infested for 22 days.
* Number of animals.

Student's test, applicable after control of the extent test makes it possible to obtain highly significant values of the decrease in the number of worms in rats immunized with the target antigens of antimony/potassium tartrate or Amphotalide $t=8.32$; $ddl=6$; $p<0.001$ and $t=4.26$; $ddl=6$; $p<0.05$.

(b) Study of the biological phenomena in immunized mice

Counting of the worms collected by hepatic perfusion.

The number of male and female worms is noted. The number of worms of the drug-control mice is not significantly different from the number of worms of the control mice. Student's test does not show significantly different values between the number of worms of the immunized mice and that of the control mice.

(c) Study of the biological phenomena in mice subjected to passive transfer of antibodies The number of male and female worms is recorded in Table III:

TABLE III

| | Male | Female | Total |
|---|---|---|---|
| Control mice receiving healthy rabbit serum (5)* | 10.60 ± 7.80 | 11 ± 10.77 | 21.60 ± 17.81 |
| Mice receiving rabbit target antigen immune serum | | | |
| -THIOSINAMINE (4) | 5.75 ± 4.27 | 7.75 ± 9.54 | 13.50 ± 13.72 |
| -ANTIMONY/POTASSIUM TARTRATE (3) | 3.67 ± 4.04 | 3.61 ± 5 | 8.67 ± 7.51 |
| -ASTIBAN (6) | 4.50 ± 5.50 | 3.83 ± 3.71 | 8.33 ± 8.69 |
| -EMETINE (7) | 2 ± 3.61 | 1.43 ± 2.51 | 3.43 ± 6.11 |

LEGEND OF TABLE III:
Average (± SD) of the number of male, female, and total worms of the mice having received the anti-target-antigen immune serum of the drugs.
*Number of animals.

Student's test shows highly significant differences between the number of worms of the control mice and that of the mice which received the rabbit anti-target antigen immune serum of Emetine.

$t=2.59$; d.d./. $=10$; $p<0.001$.

The concept and the procedure employed are capable of being extended to the field of parasitic and infectious diseases in general.

I claim:

1. A method of preparing an antischistosomic immunological agent from human or animal schistosomes, comprising the steps of
    obtaining a total extract of antigens of schistosomes, the antigens being target antigens of the schistosomes with respect to a schistosomicidal drug,
    contacting a schistosomicidal drug, which is a ligand, with the total extract, whereby the target antigens become fixed on the drug as target antigens bound to the ligand.

2. The method as set forth in claim 1, further comprising the step of
    separating the target antigens from said drug.

3. The method as set forth in claim 1, further comprising the step of
    immobilizing the schistosomicidal drug on an insoluble support in an affinity chromatography step, whereby the target antigens are retained as antigens bound to the ligand on the support,
    separating the target antigens from the ligands on the support by elution with a solvent to obtain free target antigens.

4. The method as set forth in claim 3, wheren
    said insoluble support constitutes Sepharose and said solvent is an acid buffer.

5. The method as set forth in claim 1, wherein
    the step of contacting is performed with a schistosomicidal drug under super-saturated conditions, whereby after the contacting step with the total extract of antigens of the schistosome, the target antigens are fixed on an insoluble ligand, and
    separating out the target antigens bound to the ligand.

6. The method as set forth in claim 5, wherein
    said step of separating is by washing with additional saturated solution of the same drug.

7. An antischistosome immunological agent comprising principally a schistosome extract constituting target antigens of a schitosomicidal drug.

8. The immunological agent according to claim 7, further comprising
    a support consisting of a schistosomicidal drug, with target antigens being fixed to said support.

9. The immunological agent as set forth in claim 8, wherein
    said support is a member of the group consisting of Niridazole, Thiosinamine, Astiban, Emetine Chlorohydrate and Amphotalide.

10. An immunological agent comprising principally a schistosome extract constituting target antigens of a schistosomicidal drug as set forth in claim 7, obtained by the steps of
    obtaining a total extract of antigens of schistosomes, the antigens being target antigens of the schistosomes with respect to a schistosomicidal drug,
    contacting a schistosomicidal drug, which is a ligand with the total extract, whereby the target antigens become fixed on the drug as target antigens bound to the ligand,
    immobilizing the schistosomicidal drug on an insoluble support in an affinity chromatography step, whereby the target antigens are retained as antigens bound to the ligand on the support.
    separating the target antigens from the ligands on the support by elution with a solvent to obtain the target antigens.

11. An immunoligical agent comprising principally a schistosome extract comprising target antigens of a schistosomicidal drug as set forth in claim 8, obtained by the steps of
    obtaining a total extract of antigens of schistosomes, the antigens being target antigens of the schistosomes with respect to a schistosomicidal drug,
    contacting a schistosomicidal drug, which is a ligand with the total extract, whereby the target antigens become fixed on the drug as target antigens bound to the ligand,
    applying the schistosomicidal drug under supersaturated conditions, whereby after the contacting step with the total extract of antigens of the schistosome, the target antigens are fixed on an insoluble ligand,
    separating out the target antigents bound to the ligand.

* * * * *